United States Patent

Shioiri et al.

Patent Number: 5,158,970
Date of Patent: Oct. 27, 1992

[54] PROLINE DERIVATIVES

[75] Inventors: Takayuki Shioiri, Aichi; Yasumasa Hamada; Naoko Irako, both of Nagoya; Kunio Kado, Tokyo, all of Japan

[73] Assignee: Kabushiki Kaisha Yakult Honsha, Tokyo, Japan

[21] Appl. No.: 476,698

[22] Filed: Feb. 8, 1990

[30] Foreign Application Priority Data

Feb. 20, 1989 [JP] Japan .................... 1-38179

[51] Int. Cl.⁵ ............ A61K 31/40; C07D 403/06
[52] U.S. Cl. .................... 514/422; 548/518; 548/539; 548/540
[58] Field of Search .......... 514/423, 422; 548/518, 548/540, 530, 539

[56] References Cited

U.S. PATENT DOCUMENTS

| | | | |
|---|---|---|---|
| 4,687,778 | 8/1987 | Tsuru et al. | 514/419 |
| 4,701,465 | 10/1987 | Tanaka et al. | 548/530 X |
| 4,743,616 | 5/1988 | Tanaka et al. | 548/540 X |
| 4,772,587 | 9/1988 | Tanaka et al. | 514/423 X |
| 4,873,342 | 10/1989 | Tanaka et al. | 548/518 |
| 4,880,827 | 11/1989 | Tamoto et al. | 548/518 X |
| 4,929,633 | 5/1990 | Shibahara et al. | 514/423 |
| 5,051,444 | 9/1991 | Tamoto et al. | 548/539 X |

FOREIGN PATENT DOCUMENTS

| | | |
|---|---|---|
| 238319 | 9/1987 | European Pat. Off. |
| 345428 | 12/1989 | European Pat. Off. |
| 60-188317 | 9/1985 | Japan . |
| 2270557 | 11/1987 | Japan .............. 548/518 |
| 62-225377 | 3/1989 | Japan . |
| 62-327181 | 7/1989 | Japan . |

OTHER PUBLICATIONS

Tetrahedron Letters, vol. 27, No. 5, Dec. 1986 pp. 6111-6114, Mori et al.

Primary Examiner—Joseph P. Brust
Attorney, Agent, or Firm—Birch, Stewart, Kolasch & Birch

[57] ABSTRACT

New proline derivatives of the general formula:

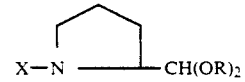

wherein R stands for a lower alkyl group and X for a N-terminal protective group conventional in amino acid chemistry or an acyl group derived from an amino acid with a protective group at the N-terminal. They have inhibitory activity against prolylendopeptidase and are relatively chemically stable as compared with known compounds of this type.

2 Claims, No Drawings

PROLINE DERIVATIVES

BACKGROUND OF THE INVENTION

1. Field of the Invention

The present invention relates to new proline derivatives useful as medicaments or intermediates therefor.

2. Description of the Prior Art

Tsuru, Yoshimoto et al. have recently revealed that those substances having a proline skeleton at their N-terminal, e.g. N-benzyloxy-carbonyl-L-prolyl-L-prolinal, have inhibitory activity to proline endopeptidase as well as an anti-amnestic action (Japanese Laid-open Patent Appln No. Sho. 60-188317 and U.S. Pat. No. 4,687,778). These substances are expected by many to open a way to the treatment of senile dementia, for example Alzheimer's dementia which is now increasing, and attempts of synthesis have been made to seek more potent proline endopeptidase inhibitors. (Japanese Patent Appln. Sho. 62-225377 and 62-327181.) Among these groups of compounds, those derivatives, with an appropriate protective group at the N-terminal, whose C-terminal takes the form of an aldehyde group, i.e. di- and mono-peptide derivatives of prolinal and thioprolinal, have been found to possess an outstanding level of such activity.

These derivatives, however, are chemically unstable, for example they are subject to oxidation due to the aldehyde group. There is therefore a demand to develop compounds of higher chemical stability for the purpose of developing medicaments for clinical use.

DETAILED DESCRIPTION OF THE INVENTION

We have succeeded, by modifying the aldehyde group in the prolinal derivatives as mentioned above into an acetal form, in synthesizing new compounds which have the above-mentioned inhibitory activity to prolylendopeptidase and which are relatively chemically stable. The present invention has been accomplished on the basis of the above finding.

Thus, the present invention provides new prolinal derivatives of the general formula:

(I)

wherein R stands for a lower alkyl group and X for a N-terminal protective group conventional in amino acid chemistry or an acyl group derived from an amino acid with a protective group at the N-terminal.

The new prolinal derivatives of the present invention may be prepared by some different methods as follows.

Thus, for example, compounds of the general formula (I) wherein X stands for a N-terminal protective group conventional in amino acid chemistry may be prepared by subjecting a prolinal dialkyl acetal of the general formula:

(II)

wherein R has the meaning as defined above, to an amino acid - N atom protection reaction known per se.

This reaction can conveniently be carried out by reacting a benzoic or succinic acid derivative or the like which corresponds to the desired protective group with a dialkyl acetal of the general formula (II) in the presence of an amide bond - forming condensation agent such as diethylphosphoryl cyanide. It is also possible to react therewith an acylation agent corresponding to the desired protective group in the presence of an appropriate acid or base as catalyst.

Alternatively, the compounds of the present invention may be prepared by treating a prolinal of the general formula:

(III)

wherein X has the meanings as defined above in or in the presence of the corresponding alcohol (ROH), using an acid catalyst.

The present invention will now be illustrated in more detail by way of Examples.

EXAMPLE 1

Preparation of p-methoxybenzoyl-L-prolinal dimethyl acetal tert-Butoxycarbonyl-L-prolinal dimethyl acetal (1.0 g, 4.08 mmol) is stirred for one hour at room temperature in 10% HCl-methanol (8.2 ml) and the mixture is evaporated to dryness under reduced pressure to give quantitatively L-prolinal dimethylacetal hydrochloride as a solid. The product is dissolved in dimethylformamide (5 ml) containing p-anisic acid (938 mg, 6.16 mmol) and diethyl-phosphoryl cyanide (0.65 ml, 8.25 mmol). To the solution is added dropwise triethylamine (1.15 ml, 8.25 mmol) under cooling and agitation in an ice-methanol bath. After the dropwise addition the mixture is stirred for one hour under cooling and then for one hour at room temperature. Benzene-ethyl acetate (2:1, 150 ml) is added to the reaction mixture and the organic layer was separated, washed successively with a saturated aqueous solution of sodium hydrogen carbonate (15 ml), water (15 ml) and a saturated aqueous solution of edible salt (15 ml), dried over sodium sulfate and filtered. The filtrate is concentrated to dryness under reduced pressure. The residue is purified by column chromatography on silica gel (n-hexane-dichloromethanemethanol, 6:4:1) to give 747 mg (65%) of the title compound as white crystals.

m.p. 51°–52.5° [ether-n-hexane].

$[\alpha]_D^{24} -115.7°$ (c=1.01, MeOH).

IR(Nujol): 2930, 1610, 1460, 1410, 1400, 1260, 1180, 1080, 1030, 850.

NMR(in CDCl$_3$): 1.45–2.40(4H,m), 3.15–3.70 and 3.50(8H,m), 3.94(3H,s), 4.20–4.60(1H,m), 4.60–5.00(1H,m), 6.90(2H,d,J=8 Hz), 7.50(2H,d,J=8 Hz).

Analysis: Calcd. (for C$_{15}$H$_{21}$NO$_4$) C 64.50; H 7.58; N 5.05. Found C 64.44; H 7.62; N 5.08.

EXAMPLE 2

Preparation of 4-p-methoxyphenylbutyryl-L-prolinal dimethyl acetal

L-prolinal dimethyl acetal hydrochloride obtained in the same manner as in Example 1 is dissolved in dimethylformamide (4 ml) containing 4-p-methoxyphenylbutyric acid (740 mg, 3.81 mmol) and diethylphosphoryl cyanide (0.48 ml, 3.16 mmol). To the solution is added dropwise triethylamine (1.15 ml, 8.25 mmol) under cooling and agitation in an ice-methanol bath. After the dropwise addition, the mixture is continued to be stirred for one hour under cooling and then for one hour at room temperature. Benzene-ethyl acetate (2:1, 150 ml) is added to the reaction mixture, and the organic layer is separated, washed successively with a saturated aqueous solution of sodium hydrogen carbonate (15 ml), water (15 ml) and a saturated aqueous solution of edible salt (15 ml), dried over sodium sulfate and filtered. The filtrate is concentrated to dryness under reduced pressure. The residue is purified by column chromatography on silica gel (benzene-ethyl acetate, 1:2→1:1) to give 727 mg (58%) of the title compound as white crystals.

IR(Nujol): 2940, 1640, 1520, 1420, 1310, 1250, 1180, 1130.

NMR(in $CDCl_3$): 1.58–3.00(10H,m), 3.00–3.66 and 3.45(8H,m,s), 3.76(1H,s), 4.00–4.51(1H,m), 4.73(1H,d,J=3 Hz), 6.76(2H,d,J=9 Hz), 7.10(2H,d,J=9Hz).

EXAMPLE 3

Preparation of N-benzyloxycarbonyl-D-prolyl-L-prolinal dimethyl acetal

L-prolinal dimethyl acetal hydrochloride obtained in the same manner as in Example 1 is dissolved in dimethylformamide (4 ml) containing tert-butoxycarbonyl-D-proline (790 mg, 3.17 mmol) and diethylphosphoryl cyanide (0.48 ml, 3.16 mmol). To the solution is added dropwise triethylamine (1.15 ml, 8.25 mmol) under cooling and agitation in an ice-methanol bath. The mixture is continued to be stirred for one hour under cooling and then for one hour at room temperature. Benzene-ethyl acetate (2:1, 150 ml) is added to the reaction mixture, and the organic layer is separated, washed successively with a saturated aqueous solution of sodium hydrogen carbonate (15 ml), water (15 ml) and a saturated aqueous solution of edible salt (15 ml), dried over sodium sulfate and filtered. The filtrate is concentrated to dryness under reduced pressure. The residue is purified by column chromatography on silica gel (benzene-ethyl acetate, 1:2→1:1) to give 713 mg (63%) of the title compound as a pale yellow syrup.

IR(Neat): 2950, 1700, 1640, 1410, 1360, 1270, 1200, 1120, 1080, 1030.

NMR(in $CDCl_3$): 1.36–2.28(8H,m), 3.02–3.82 and 3.48(10H,m), 3.82–4.34(2H,m), 4.34–4.86(1H,m), 4.86–5.36(2H,m), 7.00–7.46(5H,m).

EXAMPLE 4

Preparation of N-tert-butoxycarbonyl-L-prolinal diethyl acetal tert-Butoxycarbonyl-L-prolinal is acetalized with methyl orthoformate in a 0.4 M solution of cerium chloride in ethanol to give tert-butoxycarbonyl-L-prolinal dimethyl acetal as a colorless syrup.

$[\alpha]_D^{23.5}$ −73.5° (c=1.03, MeOH).

IR(Neat): 2980, 1690, 1380, 1170, 1110, 1060.

NMR(in $CDCl_3$): 1.02–1.32(6H,m), 1.48 and 1.60–2.28(13H,s,m), 3.12–4.02(7H,m), 4.72(1H,d,J=16 Hz).

EXAMPLE 5

Preparation of N-p-methoxybenzoyl-L-prolinal diethyl acetal p-Anisoyl chloride is obtained as a pale pink oil from reaction of p-anisic acid with thionyl chloride in methylene chloride.

IR(Neat): 1760, 1740, 1600, 1570, 1500.

NMR(in $CDCl_3$): 3.84(3H,s), 6.87(2H,d,J=9 Hz), 7.97(2H,d,J=9 Hz).

L-prolinal diethyl acetal hydrochloride is prepared in the same manner as described in Example 1 and dissolved, together with the p-anisoyl chloride (679 mg, 3.98 mmol) prepared as mentioned above, in methylene chloride (12 ml), and triethylamine (1.7 ml, 12.2 mmol) is added dropwise thereto under ice-cooling and agitation. After the dropwise addition, stirring is further continued for 30 minutes under cooling and ether (40 ml) is added to the reaction mixture. The ethereal layer is separated, washed successively with a saturated aqueous solution of sodium hydrogen carbonate and a saturated aqueous solution of edible salt, dried over sodium sulfate and filtered. The filtrate is concentrated to dryness under reduced pressure. The residue is purified by column chromatography on silica gel (benzene:ether, 2:1) to give 687 mg (56%) of the title compound as pale yellow crystals.

IR(Neat): 3000, 1630, 1580, 1520, 1430, 1410, 1310, 1260.

NMR(in $CDCl_3$): 1.20(6H,t,J=6 Hz), 1.50–2.30(4H,m), 3.28–3.67(6H,m), 3.73(3H,s), 4.03–4.50(1H,m), 4.50–5.00(1H,m) 6.78(2H,d,J=9 Hz), 7.38(2H,d,J=9 Hz).

EXAMPLE 6

Preparation of N-o-methoxybenzoyl-L-prolinal diethyl acetal o-Anisoyl chloride is obtained from o-anisic acid and thionyl chloride in a manner similar to that as mentioned in Example 5 for the preparation of p-anisoyl chloride.

IR(Neat): 2950, 1780, 1650, 1575, 1480, 1430, 1290, 1260.

NMR(in $CDCl_3$): 3.88(3H,s), 6.80–8.17(4H,m).

L-prolinal diethyl acetal hydrochloride is dissolved, together with the o-anisoyl chloride (853 mg, 4.01 mmol), in methylene chloride (12 ml), and triethylamine (1.7 ml, 12.2 mmol) is added dropwise thereto under ice-cooling and agitation. After the dropwise addition, stirring is further continued for 30 minutes under cooling and then for one hour and a half at room temperature. Ether (40 ml) is added to the reaction mixture, and the ethereal layer is separated, washed with a saturated aqueous solution of sodium hydrogen carbonate and a saturated aqueous solution of edible salt, dried over sodium sulfate and filtrated. The filtrate is concentrated to dryness under reduced pressure. The residue is purified by column chromatography on silica gel (n-hexane-ethyl acetate, 2:1) to give 952 mg (75%) of the title compound as a pale yellow syrup.

IR(Neat): 2980, 1630, 1610, 1500, 1460, 1440, 1420, 1380, 1350.

NMR(in CDCl$_3$): 0.80–1.13(6H,m), 1.63–2.63(4H,m),2.83–4.00 and 3.30(9 H,m,s), 4.00–4.87 and 5.10(2H,m,d,J=2 Hz), 6.77–7.50(4H,m).

EXAMPLE 7

Preparation of N-(4-p-methoxyphenylbutyryl)-L-prolinal diethyl acetal

L-prolinal diethyl acetal hydrochloride is dissolved, together with 4-(p-methoxyphenyl)butyryl chloride (686 mg, 4.02 mmol) prepared in the same manner as described in Example 5, in methylene chloride (12 ml) and triethylamine (1.7 ml, 12.2 mmol) is added dropwise thereto under ice-cooling and agitation. After the dropwise addition, stirring is further continued for 30 minutes under cooling, and then for one hour at room temperature. Ether (40 ml) is added to the reaction mixture, and the ethereal layer is separated, washed with a saturated aqueous solution of sodium hydrogen carbonate and a saturated aqueous solution of edible salt, dried over sodium sulfate and filtered. The filtrate is concentrated to dryness under reduced pressure. The residue is purified by column chromatography on silica gel (n-hexane-ethyl acetate, 2:1) to give 805 mg (58%) of the title compound as a pale yellow syrup.

IR: 2950, 1640, 1520, 1420, 1300, 1200.

NMR(in CDCl$_3$): 0.84–1.50(6H,m), 1.50–2.78(10H,m),2.78–3.90 and 3.73(9H,m), 3.90–4.30(1H,m), 4.83(1H,d,J=9 Hz), 6.70(2H,d,J=9 Hz), 7.00(2H,d,J=9 Hz).

EXAMPLE 8

Preparation of N-benzyloxycarbonyl-L-prolyl-L-prolinal diethyl acetal

To a solution of L-prolinal diethyl acetal hydrochloride (898 mg) and benzyloxycarbonyl-L-proline (1.2 g, 4.82 mmol) in dichloromethane (15 ml) are added successively, under ice-cooling and agitation, 1-hydroxybenzotriazole (645 mg), triethylamine (0.68 ml, 4.88 mmol) and N,N-dicyclohexylcarbodiimide (1.0 g, 4.90 mmol). After the addition, stirring is further continued for 2 hours under ice-cooling, and then for 45 minutes at room temperature. Ether (40 ml) is added to the reaction mixture and the mixture is filtered for removal of insolubles. The filtrate is washed successively with water (10 ml), a saturated aqueous solution of sodium hydrogen carbonate (10 ml) and a saturated aqueous solution of edible salt (10 ml), dried over magnesium sulfate and filtered. The filtrate is concentrated to dryness under reduced pressure. The residue is purified by column chromatography on silica gel (benzene-ether-ethanol, 20:20:1) to give 1.125 g (69%) of the title compound as pale yellow crystals.

m.p. 58.5°–61° [ether-n-hexane].

$[\alpha]_D^{24.5}$ −106.6° (c=0.98, MeOH).

IR(Nujol): 2950, 1700, 1640, 1460, 1410, 1380, 1350.

NMR(in CDCl$_3$): 0.40–0.72(6H,m), 0.72–2.60(8H,m), 2.60–3.96(8H,m), 3.96–5.36(5H,m), 7.00–7.48(5H,m).

Analysis: Calcd. (for C$_{23}$H$_{32}$N$_2$O$_5$) C 65.32; H 7.97; N 6.93. Found C 65.29; H 8.03; N 6.95.

EXAMPLE 9

Preparation of N-benzyloxycarbonyl-D-prolyl-L-prolinal diethyl acetal

L-prolinal diethyl acetal hydrochloride (726 mg) and benzyloxycarbonyl-D-proline (801 mg, 3.22 mmol) are used to prepare 942 mg (73%) of the title compound as a pale yellow syrup in a manner similar to that as mentioned in Example 8.

IR(Neat): 2980, 1710, 1650, 1420, 1360, 1170, 1120, 1060.

NMR(in CDCl$_3$): 1.20(6H,t,J=7 Hz), 1.50–2.50(8H,m), 3.01–4.00(8H,m), 4.00–4.68 and 4.90(3H,m,d,J=2 Hz), 4.97–5.22(2H,m), 7.18–7.40(5H,m).

EXAMPLE 10

Preparation of N-tosylsarcosyl-L-prolinal dimethyl acetal

N-tosylsarcosine (60 g, 247 mmol) and L-prolinol (24.9 g, 247 mmol) are dissolved in methylene chloride (800 ml), and triethylamine (102.5 ml, 741 mmol) is added thereto. To this mixture is added dropwise, over a period of one hour under water-cooling, a solution of 2-chloro-1,3-dimethylimidazolium chloride (DMC) (62.6 g, 371 mmol) in methylene chloride. The mixture is further stirred for 2 hours at room temperature and then the reaction liquid is washed successively with water (1 l, a saturated aqueous solution of sodium hydrogen carbonate (1 l, 1N hydrochloric acid (1 l) and water (1 l). The organic layer is dried over anhydrous magnesium sulfate and filtered, and the filtrate is concentrated to dryness under reduced pressure to give N-tosylsarcosyl-L-prolinol (82.1 g, 102%).

In the next step, a solution of dimethyl sulfoxide (DMSO) (35.3 ml, 0.491 mol) in methylene chloride (970 ml) is added dropwise, over a period of 2.5 hours at −60° C. under an atmosphere of nitrogen, to a solution of oxalyl chloride (44.7 ml, 0.491 mol) in methylene chloride (970 ml), and the mixture is stirred for a further five minutes. A solution of N-tosylsarcosyl-L-prolinol (80 g, 0.245 mol) in methylene chloride (950 ml) is then added dropwise to the mixture over a period of 75 minutes, and the mixture is stirred for a further thirty minutes. Triethylamine (348 ml, 2.45 mol) is then added dropwise thereto over a period of ten minutes, and the mixture is stirred for a further ten minutes. After brought back to room temperature, the mixture is washed with water (2 1×2) and the organic layer is concentrated to dryness under reduced pressure. The residue is dissolved in ethanol (320 ml), and the solution is vigorously stirred for 15 minutes after addition of a saturated aqueous solution of sodium hydrogen carbonate (250 ml) and water (438 ml). The ethanol is then distilled off under reduced pressure, and water (600 ml) is added to the residue. The mixture is extracted with chloroform (300 ml) and ether (500 ml×2) and the organic layers are discarded. The aqueous layers are adjusted with potassium carbonate to a pH higher than 10 and extracted with chloroform. The organic layer is separated, washed successively with water (500 ml×2), 1N hydrochloric acid (500 ml) and water (500 ml), dried over anhydrous magnesium sulfate and concentrated to dryness under reduced pressure to give N-tosylsarcosyl-L-prolinal (49.5 g, 62.3%).

m.p. 111.0° C.

Optical rotation $[\alpha]_D^{22} = -48.95°$ (c=1, CHCl$_3$)

IR(KBr)cm$^{-1}$: 3440, 2990, 2920, 2810, 1730, 1640, 1445, 1335, 1160.

NMR(in CDCl$_3$)δ ppm: 1.90–2.20(4H,m), 2.42(3H,s), 3.61(3H,s), 3.40–4.10(4H,m), 4.44(1H,br,t), 7.23(2H,d,J=11 Hz), 7.62(2H,d,J=11 Hz), 9.38(1H,s).

In the next step, under an atmosphere of nitrogen, N-tosylsarcosyl-L-prolinal (10 g, 30 9 mmol) is vigorously stirred (for 4 hours) together with absolute methanol (75 ml), anhydrous cation-exchange resin (S-100) (3.8 g) and calcined sodium sulfate (10 g). The mixture is filtered to remove insolubles and washed with methanol and dioxane. The combined filtrate is concentrated to dryness under reduced pressure. The residue is purified by column chromatography on silica gel (n-hexane:methylene chloride:methanol=6:4:1) to give the title compound (9 g, 78.9%).

Optical rotation $[\alpha]_D^{23} = -30.12°$

IR(KBr)cm$^{-1}$: 3600, 3490, 2950, 1660, 1445, 1340, 1162, 1064.

NMR(in CDCl$_3$)δ ppm: 1.75–2.30(4H,m), 2.50(3H,s), 2.89(3H,s), 3.46(3H,s), 3.51(3H,s), 3.65–4.25(5H,m), 4.72(1H,br,d), 7.31(2H,d,J=11 Hz), 7.72(2H,d,J=11 Hz).

EXAMPLE 11

Preparation of N-benzyloxysuccinyl-L-prolyl-L-prolinal diethyl acetal

N-(benzyloxysuccinyl)-L-proline (152.5 g, 0.5 mol), L-prolinol (50.5 g, 0.5 mol) and triethylamine (200 ml) are dissolved in methylene chloride (2 l), and a solution of DMC (127 g, 0.75 mol) in methylene chloride (500 ml) is added dropwise thereto over a period of 40 minutes under water-cooling. The mixture is stirred for a further three hours at room temperature. The reaction liquid is washed successively with water (1 l), a saturated aqueous solution of sodium hydrogen carbonate (1 l), 1N hydrochloric acid (1 l) and water (1 l), and the organic layer is dried over anhydrous magnesium sulfate and filtered. The filtrate is concentrated to dryness under reduced pressure and the residue is purified by column chromatography on silica gel (chloroform:methanol) to give N-(benzyloxysuccinyl)-L-prolyl-prolinol (90 g, 46.4%).

This prolinol derivative (63.5 g, 164 mmol) is subjected to oxydation reaction in the same manner as in Example 10 to give the corresponding N-(benzyloxysuccinyl)-L-prolyl-L-prolinal (26.1 g, 41.4%).

Optical rotation $[\alpha]_D^{23} = -91.97°$

IR(KBr)cm$^{-1}$: 3400, 2960, 1720, 1620, 1430, 1200.

NMR(in CDCl$_3$)δ ppm: 1.90–2.30(8H,br), 2.70(4H,br), 3.40–3.80(4H,m), 4.40–4.70(2H,m), 5.22(2H,s), 7.28(5H,s), 9.45(1H,s).

This prolinal derivative (10 g, 25.9 mmol) is acetalized in dry ethanol likewise in the same manner as in Example 10 to give the title compound (8.5 g, 71.4%).

NMR(in CDCl$_3$)δ ppm: 1.05–1.35(6H,m), 1.85–2.26(8H,br), 2.73(4H,br,s), 3.30–3.90(8H,m), 4.25(1H,br), 4.60–4.95(2H,m), 5.13(2H,s), 7.32(5H,s).

EXAMPLE 12

Preparation of N-succinyl-L-prolyl-L-prolinal diethyl acetal

N-(benzyloxysuccinyl)-L-prolyl-L-prolinal diethyl acetal (17.1 g, 37.2 mmol) is subjected to catalytic reduction at normal pressure at room temperature for 20 hours in dry dioxane (100 ml) in the presence of 5% Pd/C of 50% water content (3.4 g). The mixture is filtered to remove the catalyst and the filtrate is concentrated to dryness under reduced pressure. The residue is purified by column chromatography on silica gel (400 g) (methylene chloride:ethanol:n-hexane=10:1:1) to give the title compound (8 g, 58.2%).

Optical rotation $[\alpha]_D^{22} = -110.73°$ (c=1, EtOH)

IR(KBr)cm$^{-1}$: 3450, 2970, 1725, 1620, 1440, 1060.

NMR(in CDCl$_3$)δ ppm: 1.30–1.40(6H,m), 2.23(8H,br), 2.43(4H,s), 3.60–3.80(8H,m), 4.50(1H,br), 4.70–5.00(2H,m), 8.57(1H,s).

EXAMPLE 13

Preparation of N-(benzyloxysuccinyl)-sarcosyl-L-prolinal diethyl acetal

N-(benzyloxysuccinyl)sarcosine (139.5 g, 0.5 mol), L-prolinol (50.5 g, 0.5 mol) and triethylamine (200 ml) are dissolved in methylene chloride (2 l), and a solution of DMC (127 g, 0.75 mol) in methylene chloride (500 ml) is added dropwise thereto under water-cooling over a period of thirty minutes. The mixture is stirred at room temperature for a further three hours, and the reaction liquid is washed successively with water (1 l), a saturated aqueous solution of sodium hydrogen carbonate (1 l), 1N hydrochloric acid (1 l) and water (1 l). The organic layer is dried over anhydrous magnesium sulfate and filtered. The filtrate is then concentrated to dryness under reduced pressure, and the residue is purified by column chromatography on silica gel (chloroform:methanol) to give N-(benzyloxysuccinyl)sarcosyl-L-prolinol (88.4 g, 48.8%).

This prolinol derivative (51.7 g, 143 mmol) is subjected to oxidation reaction in accordance with the same method as in Example 10 to give the corresponding prolinal derivative (19.6 g, 38.1%).

NMR(in CDCl$_3$)δ ppm: 1.95–2.35(4H,m), 2.82(4H,s), 3.23(3H,s), 3.48–3.85(2H,m), 4.20–4.65(3H,m), 5.19(2H,s), 7.36(5H,s), 9.50(1H,s).

This prolinal derivative (10 g, 27.8 mmol) is acetalized in dry ethanol likewise in the same manner as in Example 10 to give the title compound (8.1 g, 67.2%).

EXAMPLE 14

Preparation of N-succinyl-sarcosyl-L-prolinal diethyl acetal

N-(benzyloxysuccinyl)sarcosyl-L-prolinal diethyl acetal (8.1 g, 18.7 mmol) obtained in Example 13 is subjected to catalytic reduction at normal pressure at room temperature for 20 hours in dry dioxane (50 ml) in the presence of 5% Pd/C of 50% water content (1.6 g). The mixture is filtered to remove the catalyst and the filtrate is concentrated to dryness under reduced pressure. The residue is purified by column chromatography on silica gel (200 g) (chloroform:ethanol=10:1) to give the title compound (5 g, 77.9%).

Optical rotation $[\alpha]_D^{20} = -32.83°$

IR(KBr)cm$^{-1}$: 3450, 2970, 1724, 1640, 1402, 1120, 1060.

NMR(in CDCl$_3$)δ ppm: 1.10–1.40(6H,m), 2.00(4H,br), 2.71(4H,s), 3.30(3H,s), 3.45–3.90(6H,m), 4.15(3H,br), 4.85–4.90(1H,m), 8.96(1H,s).

EXAMPLE 15

Preparation of N-(benzyloxysuccinyl)-L-pyroglutamyl-L-prolinal diethyl acetal

L-pyroglutamic acid (100 g, 0.775 mol), L-prolinol (78.3 g, 0.775 mol) and triethylamine (322 ml) are dissolved in methylene chloride (2.5 l), and a solution of DMC (196.5 g, 1.163 mol) in methylene chloride (600 ml) is added dropwise over a period of forty minutes under water-cooling. The mixture is stirred for a further 3 hours at room temperature, and the reaction liquid is filtered to remove insolubles. The filtrate is concentrated to dryness under reduced pressure, and the residue is crystallized from dioxane-ether to give L-pyroglutamyl-L-prolinol (38.4 g, 23.3%).

The thus obtained L-pyroglutamyl-L-prolinol (110 g, 0.519 mol) and dihydropyran (220 g, 2.62 mol) are dissolved in acetonitrile (2.75 l), and pyridine toluenesulfonate (11 g) is added under water-cooling. The mixture is stirred at room temperature for two days, and the reaction liquid is concentrated under reduced pressure, dissolved again in methylene chloride (1.5 l) and washed successively with 5% potassium carbonate (1 l) and water (1 l). The methylene chloride layer is dried over anhydrous magnesium sulfate and filtered. The filtrate is concentrated to dryness under reduced pressure to give N-pyroglutamyl-O-tetrahydropyranyl-L-prolinol (169 g, 110%).

The thus obtained tetrahydropyranyl derivative (140 g, 0.473 mol) is dissolved in dry benzene (1.4 l). Sodium hydride (22.8 g, 0.523 mol) is added thereto under ice-cooling and the mixture is stirred at room temperature for 15 minutes. A solution of benzyloxysuccinyl-p-nitrophenol (156.8 g, 0.476 mol) in benzene (1.1 l) is added dropwise thereto over a period of twenty minutes, and the mixture is stirred overnight at room temperature. Insolubles are filtered off and the filtrate is concentrated to dryness under reduced pressure. The residue is purified by column chromatography on silica gel (1 kg) (chloroform-methanol) to give N-(benzyloxysuccinyl-pyroglutamyl)-O-tetrahydropyranyl-L-prolinol (82 g, 35.7%).

The thus obtained benzyloxysuccinyl-tetrahydropyranyl derivative (155.6 g, 0.32 mol) is stirred in a mixed solvent of glacial acetic acid/tetrahydrofuran/water (1.5 l/520 ml/520 ml) for 1.5 hours at room temperature and then for one hour at 45° C. The mixture is then concentrated under reduced pressure, and water (1 l) is added to the concentrate. The mixture is then adjusted to pH 6.7 with a saturated aqueous solution of sodium hydrogen carbonate and extracted with methylene chloride (1 l). The methylene chloride layer is dried over anhydrous magnesium sulfate and filtered, and the filtrate is concentrated to dryness under reduced pressure. The residue is crystallized from ether to give N-benzyloxysuccinylpyroglutamyl-prolinol (85 g, 66.1%).

The thus obtained prolinol derivative (38 g, 94.5 mmol) is subjected to oxidation reaction in the same manner as in Example 10 to give the corresponding prolinal derivative (23.9 g, 63.2%).

NMR(in CDCl$_3$)δ ppm: 1.90-2.35(4H,m), 2.55-2.82(4H,m), 3.10-3.90(4H,m), 4.61(1H,br t), 4.82-5.00(1H,m), 5.12(2H,s), 7.31(5H,s), 9.49(1H,s).

The resultant prolinal derivative (23.9 g, 59.8 mmol) is acetalized in dry ethanol likewise in accordance with the same method as in Example 10 to give the title compound (18.2 g, 64.3%).

NMR(in CDCl$_3$)δ ppm: 1.05-1.35(6H,m), 1.80-2.35(6H,m), 4.28(1H,br), 4.80-4.95(2H,m), 5.21(2H,s), 7.30(5H,s).

EXAMPLE 16

Preparation of N-succinyl-L-pyroglutamyl-L-prolinal diethyl acetal

N-(benzyloxysuccinyl)pyroglutamyl-L-prolinal diethyl acetal (18 g, 38 mmol) synthesized in Example 15 is subjected to catalytic reduction at normal pressure at room temperature for 20 hours in dry dioxane (110 ml) in the presence of 5% Pd/C of 50% water content (3.6 g). The mixture is filtered to remove the catalyst and the filtrate is subjected to crystallization from n-hexane to give the title compound (10.8 g, 74%).

m.p. 153.0° C.
Optical rotation $[α]_D^{20} = -84.98°$
IR(KBr)cm$^{-1}$: 3130, 2960, 1735, 1620, 1372, 1165, 1042.
NMR(in CDCl$_3$)δ ppm: 1.02-1.62(6H,m), 1.85-2.40(6H,m), 2.50-2.80(4H,m), 3.15-3.90(8H,m), 4.20(1H,br), 4.80-5.00(2H,m), 10.02(1H,s).

The compounds of the invention obtained in the foregoing Examples were assayed for their prolylendopeptidase inhibition activity. This assay for prolylendopeptidase inhibition was carried out in accordance with the method of Yoshimoto and Tsuru (Yoshimoto, T. and Tsuru, D., Agr. Biol. Chem. Vol. 42, 2417, 1978). The corresponding number of test tubes to the number of the compounds to be tested were prepared and 2.5 mM Z-glycyl-proline-β-naphthylamide (0.25 ml), 0.1 M phosphate buffer (pH 7.0, 0.99 ml) and a solution of one of the peptides of the invention (0.1 ml) were placed in each test tube and warmed at 37° C. for 3 minutes. 0.1 ml of solution of propylendopeptidase (0.2 unit/ml) was added to each test tube. After reaction at 35° C. for 10 minutes, 1 M acetate buffer containing Triton X-100 (pH 4.0) was added to a final concentration of 10% and after the mixture was left to stand at room temperature for 15 minutes the absorbance (a) at 410 nm was measured.

The above-mentioned procedure was followed in the same manner but using buffers only in place of the solution of each compound of the invention, and the absorbance (b) was measured. The inhibition rate was determined by the following equation, with the results shown as inhibition constant (Ki) in Table 1, in whose column for "Compound" the example number where the compound was obtained is indicated:

TABLE 1

| $[(b - a)/b] \times 100$ | |
|---|---|
| Compound (indicated as the corresponding Example No.) | Ki (M) |
| Example 8 | $2.2 \times 10^{-6}$ |
| Example 3 | $4.3 \times 10^{-4}$ |
| Example 12 | $3.7 \times 10^{-4}$ |
| Example 14 | $1.0 \times 10^{-3}$ |
| Example 16 | $1.0 \times 10^{-3}$ |

As will be apparent from these results, the compounds of the present invention are active as prolylendopeptidase inhibitor and therefore possible use as anti-amnestic agent or starting materials for developing such agent can be expected of these substances.

The anti-amnestic effect of the proline derivatives of the general formula (I) mentioned above was demonstrated by the experimental method as follows.

Experimental method

A step-down passive avoidance test on rats was used as the method of assay for anti-amnestic activity to estimate the preventive effect of prolylendopeptidase inhibitors on scopolamine-induced amnesia. This method of assay involved application of electric shocks to animals upon their stepping down on a grid floor to see whether they have learned that such shocks can be avoided by staying on a platform. A passive avoidance test chamber used in this experiment was comprised of an electrifiable grid floor (20 cm in length and 22 cm in width) and a platform (20 cm in length, 15 cm in width and 5 cm in height) placed at the right back corner thereof.

5-Weeks-old male rats of Wister strain weighing 100-150 g (purchased from Japan Clea Co., Ltd.) were used in the test.

Each test compound used in the doses indicated in Tables 2-3 was dissolved or suspended in 4% gum arabic-containing distilled water (1 ml) and administered p.o. one hour before the commencement of acquisition trial. In addition, scopolamine hydrobromide dissolved in saline (0.5 ml) was intraperitoneally administered in a dose of 0.5 mg/kg 30 minutes before the acquisition trial to prepare experimental animal models of amnesia.

In the acquisition trial, the rat was placed on the platform in the test chamber and, when the animal stepped down on the grid floor, the electric current of 5.0 mA was immediately sent to the grid floor continuously until the animal went up on the platform If the rat having gone up on the platform stayed there for more than 30 seconds, the animal was regarded to have learned the situation and taken out of the test chamber. A total time of measurement in the acquisition trial was limited to 300 seconds as maximum, and the time elapsing until the rat learned the situation was measured. In order to avoid any significant difference in the rats, those which took more than 300 seconds for the learning were excluded from the experiment.

The retention trial was carried out 24 hours after the acquisition trial. In this trial, the rat was placed again on the platform in the test chamber, the time elapsing until the animal stepped down onto the grid floor (the step-down latency) was measured.

The results are shown in Tables 2 and 3. In each of these tables they are indicated as relative step-down latency, shown by each test compound-treated group in the retention trial, to step-down latency for scopolamine-treated group (i.e. test compound-treated group's step-down latency/scopolamine-treated group's step-down latency).

Abbreviations used to indicate test compounds in Table 2 are as follows:

ZPP: Benzyloxycarbonyl-L-prolyl-L-prolinal (control)
ZPPM: Benzyloxycarbonyl-D-prolyl-L-prolinal dimethyl acetal (compound of Example 3)
ZPPE: Benzyloxycarbonyl-L-prolyl-L-prolinal diethyl acetal (compound of Example 8)

TABLE 2

Anti-amnestic effect of the test compounds by oral administration in retention trial

| Test compound | Dose (mg/kg, p.o.) | Scopolamine treatment (mg/kg, i.p.) | Relative step-down latency in retention trial (mean ± S.E.) |
|---|---|---|---|
| Saline (control) | — | — | 5.7 ± 1.3 |
| Scopolamine (control) | — | 0.5 | 1.0 ± 0.3 |
| ZPP | 1 | 0.5 | 2.8 ± 1.3 |
| ZPP | 5 | 0.5 | 8.5 ± 1.6** |
| ZPP | 25 | 0.5 | 1.4 ± 0.8 |
| ZPP | 50 | 0.5 | 0.5 ± 0.1 |
| ZPP | 100 | 0.5 | 1.3 ± 0.8 |
| Saline (control) | — | — | 5.1 ± 1.1 |
| Scopolamine (control) | — | 0.5 | 1.0 ± 0.3 |
| ZPPM | 1 | 0.5 | 1.1 ± 0.3 |
| ZPPM | 5 | 0.5 | 0.7 ± 0.1 |
| ZPPM | 25 | 0.5 | 1.4 ± 0.5 |
| ZPPM | 50 | 0.5 | 0.9 ± 0.4 |
| ZPPM | 100 | 0.5 | 1.6 ± 0.5 |
| Saline (control) | — | — | 4.5 ± 0.9 |
| Scopolamine (control) | — | 0.5 | 1.0 ± 0.3 |
| ZPPE | 1 | 0.5 | 2.0 ± 0.5 |
| ZPPE | 5 | 0.5 | 0.9 ± 0.2 |
| ZPPE | 25 | 0.5 | 1.2 ± 0.3 |
| ZPPE | 50 | 0.5 | 0.7 ± 0.3 |
| ZPPE | 100 | 0.5 | 0.6 ± 0.3 |

Significantly different from scopolamine-treated group. **$p < 0.01$ (Mann-Whitney's U-test)

TABLE 3

Anti-amnestic effect of aniracetam by oral administration in retention trial

| Test compound | Dose (mg/kg, p.o.) | Scopolamine treatment (mg/kg, i.p.) | Relative step-down latency in retention trial (mean ± S.E.) |
|---|---|---|---|
| Saline (control) | — | — | 4.9 ± 0.7 |
| Scopolamine (control) | — | 0.5 | 1.0 ± 0.3 |
| aniracetam | 12.5 | 0.5 | 1.1 ± 0.4 |
| aniracetam | 25 | 0.5 | 1.6 ± 0.6 |
| aniracetam | 50 | 0.5 | 2.3 ± 0.6* |
| aniracetam | 100 | 0.5 | 0.7 ± 0.3 |

Significantly different from scopolamine-treated group. *$p < 0.05$ (Mann-Whitney's U-test)

From these and other test results, it has become evident that the compounds of the general formula (I) mentioned above possess an excellent anti-amnestic action and are thus widely utilizable as low-toxicity medicaments for the remedy of memory disorders such as senile dementia of Alzheimer's type.

The administration of the anti-amnestic compounds of the present invention may be effected in various ways, for example by injection such as intravenous, subcutaneous or intramuscular injection or by the oral route. Oral or intravenous administration is particularly preferred. The daily dose of these compounds is preferably between 1 mg and 900 mg, particularly between 5 mg and 500 mg in the case of oral administration, and between 0.5 mg and 500 mg, particularly between 1 mg and 200 mg in the case of intravenous administration.

The preparation of anti-amnestic dosage forms in accordance with the present invention may be effected by any method conventionally used for preparing different pharmaceutical preparations, the choice of appropriate such method being dependent upon the type of the desired dosage form. Examples of such preparations include forms appropriate for oily substances to be absorbed through the gastrointestinal tract, preferably soft capsules and oral liquid preparations.

Soft capsules for oral administration are a unit dosage form and may contain solubilizers such as macrogol and propylene glycol, preservatives such as ethyl p-hydroxybenzoate, propyl p-hydroxybenzoate and sorbic acid, and optionally flavoring agents, dyestuffs, aromatics and the like.

Liquid preparations for oral administration include aqueous or oily suspensions, solutions, syrups, elixirs and the like. Such liquid preparations may contain any additives customary in the art, for example, suspending agents such as sorbit syrup, methyl cellulose, gelatin, hydroxyethyl cellulose, carboxymethyl cellulose, aluminum stearate gel or hydrogenated edible fats; emulsifying agents such as lecithin, sorbitan monoleate and gum arabic (acacia); non-aqueous vehicles such as almond oil, fractionated coconut oil, oily esters, propylene glycol and ethyl alcohol; antiseptics such as methyl p-hydroxybenzoate, propyl p-hydroxybenzoate and sorbic acid; and optionally dyestuffs, aromatics and the like.

Preparations for injection may be in form of ampoules with unit doses, or contained, optionally together with such additives as antiseptics and solubilizers, in a multiple-dose container. Such preparations may take any dosage form, such as suspension, solution and emulsion in oily or aqueous vehicles, and contain such additives as suspending agents.

In the anti-amnestic agents of the present invention, the compounds of the general formula (I) mentioned above as active ingredient will generally be contained in concentrations of not less than 0.1%, preferably 1–50% by weight, depending upon the dosage form used.

The following examples illustrate the preparation of the anti-amnestic agents of the present invention, although it is not limited to these examples.

EXAMPLE OF PHARMACEUTICAL PREPARATION 1

Injection preparations
(1) Recipe

| | |
|---|---|
| N-Benzyloxycarbonyl-L-prolyl-L-prolinal dimethyl acetal | 10 mg |
| Hardened castor oil polyoxyethylene 60 mol ether | 40 mg |
| Sorbitan monostearate | 2 mg |
| Propylene glycol | 60 mg |
| Refined soybean lecithin | 2 mg |
| Cholesterol | 1 mg |
| Glucose | 50 mg |
| Distilled water | to make 1 ml |

(2) Preparation

N-Benzyloxycarbonyl-L-prolyl-L-prolinal dimethyl acetal, hardened castor oil polyoxyethylene 60 mol ether, sorbitan monostearate, propylene glycol, refined soybean lecithin and cholesterol are mixed and fused to form a homogeneous liquid in a water bath heated at about 80° C. To this liquid is added with stirring distilled water heated at about 80° C. to form a solubilized homogeneous system. Glucose is then added and distilled water is added to make the volume of 1 ml. The liquid is subjected to sterilizing filtration, and charged into an amber ampoule which is then sealed.

EXAMPLE OF PHARMACEUTICAL PREPARATION 2

Soft capsulated preparations
(1) Recipe

| | |
|---|---|
| N-Benzyloxycarbonyl-L-prolyl-L-prolinal diethyl acetal | 20 mg |
| Macrogol 400 | 350 mg |
| Propylene glycol | 38 mg |
| Dipotassium glycyrrhizinate | 1 mg |
| Menthol oil | 1 mg |
| Gelatin | 122 mg |
| Glycerol | 30.5 mg |
| D-Sorbitol liquid | 12.2 mg |
| Ethyl p-hydroxybenzoate | 0.8 mg |
| Propyl p-hydroxybenzoate | 0.5 mg |

(2) Preparation

N-Benzyloxycarbonyl-L-prolyl-L-prolinal diethyl acetal, Macrogol 400, dipotassium glycyrrhizinate, menthol oil and propylene glycol are homogeneously blended to form a suspension. Separately, a coating agent for soft capsules is manufactured from gelatin, glycerol, D-sorbitol liquid, ethyl p-hydroxybenzoate and propyl p-hydroxybenzoate. Using the suspension and the coating agent, a soft capsule is prepared.

It is understood that the preceding representative examples may be varied within the scope of the present specification both as to reactants, reaction conditions and ingredients to be blended, by one skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. A proline derivative, N-benzyloxycarbonyl-L-prolyl-L-prolinal diethyl acetal, of the structural formula:

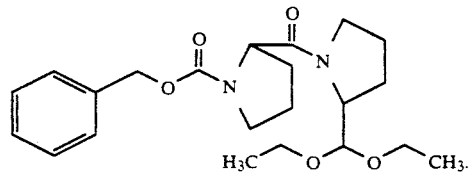

2. A pharmaceutical composition comprising an active ingredient an effective anti-amnesiac amount of the compound of claim 1.

* * * * *